United States Patent
Miller et al.

(10) Patent No.: US 10,280,101 B2
(45) Date of Patent: May 7, 2019

(54) WATER SOLUBLE CHAIN TRANSFER AGENTS

(71) Applicant: The Lubrizol Corporation, Wickliffe, OH (US)

(72) Inventors: Cory G. Miller, Sagamore Hills, OH (US); Hyungsoo Kim, Hudson, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 15/566,445

(22) PCT Filed: Apr. 22, 2016

(86) PCT No.: PCT/US2016/028787
§ 371 (c)(1),
(2) Date: Oct. 13, 2017

(87) PCT Pub. No.: WO2016/182711
PCT Pub. Date: Nov. 17, 2016

(65) Prior Publication Data
US 2018/0111900 A1    Apr. 26, 2018

Related U.S. Application Data

(60) Provisional application No. 62/158,600, filed on May 8, 2015.

(51) Int. Cl.
| | |
|---|---|
| C02F 5/10 | (2006.01) |
| C02F 1/68 | (2006.01) |
| C02F 1/58 | (2006.01) |
| C08F 220/58 | (2006.01) |
| C08F 120/58 | (2006.01) |
| C07C 329/00 | (2006.01) |
| C02F 1/00 | (2006.01) |
| C07C 329/06 | (2006.01) |
| C08F 293/00 | (2006.01) |
| C08F 120/56 | (2006.01) |
| C08F 4/08 | (2006.01) |
| C08F 22/02 | (2006.01) |

(52) U.S. Cl.
CPC ............... *C02F 5/10* (2013.01); *C02F 1/58* (2013.01); *C02F 1/683* (2013.01); *C07C 329/00* (2013.01); *C08F 120/58* (2013.01); *C08F 220/58* (2013.01); *C02F 1/00* (2013.01); *C07C 329/06* (2013.01); *C08F 4/083* (2013.01); *C08F 22/02* (2013.01); *C08F 120/56* (2013.01); *C08F 293/005* (2013.01); *C08F 2220/585* (2013.01); *C08F 2438/03* (2013.01)

(58) Field of Classification Search
None
See application file for complete search history.

(56) References Cited

U.S. PATENT DOCUMENTS

| | | | |
|---|---|---|---|
| 1,939,692 A | 12/1933 | Hardman | |
| 3,860,641 A | 1/1975 | Zengel et al. | |
| 2006/0111534 A1 | 5/2006 | Suau et al. | |
| 2006/0223936 A1 | 10/2006 | Such et al. | |
| 2009/0005529 A1 | 1/2009 | Lai | |
| 2009/0082535 A1* | 3/2009 | Nakano | C02F 5/12 526/234 |
| 2010/0105832 A1 | 4/2010 | Csihony et al. | |
| 2014/0088250 A1 | 3/2014 | Suau et al. | |
| 2015/0203653 A1 | 7/2015 | Rentsch et al. | |

FOREIGN PATENT DOCUMENTS

| | | | |
|---|---|---|---|
| CN | 102070742 B | 1/2013 | |
| CN | 102504071 B | 12/2013 | |
| WO | 2005095466 A1 | 10/2005 | |
| WO | WO-2014048856 A1 * | 4/2014 | ............ D21H 17/63 |
| WO | 2015079140 A1 | 6/2015 | |
| WO | 2015092186 A1 | 6/2015 | |

OTHER PUBLICATIONS

E. Campaigne et al., "Dithiolium Derivatives. II Some New 1,3-Dithiolim Perchlorates 1", The Journal of Organic Chemistry, vol. 28, No. 7, Jul. 1954, pp. 1708-1710.

K.A. Jensen et al., "Organic Selenium Compounds. XIV. Assignment of the C=Se Stretching Frequency of Dialkyl Diselenocarbonates," ACTA Chemia Scandinavica, vol. 24, Jan. 2070, pp. 2055-2060.

M.M. Orlinskii et al., "Synthesis and biological activity of noncondensed thiazolidones-2 with polymethylene bridges," Pharmaceutical Chemistry Journal, vol. 28, No. 4, Apr. 1994, pp. 243-245.

Christlieb M et al., "The exocyclic functionalization of bis(thiosemicarbazonate) complexes of zinc and copper: the synthesis of monomeric and dimeric species", Dalton Translations:The International Journal for Inorganic , Organometallic and Bioinorganic Chemistry, Royal Society of Chemistry, GB, Jan. 2007, pp. 5043-5054.

Shude Xiao et al., "Bifunctional 2-(alkoxycarbonothioylthio)acetic acids for the systhesis of TiO 2-poly(vinyl acetate) nanocomposites via RAFT polymerization", Journal of Polymer Science Part A: Polymer Chemistry, vol. 52, No. 5, Mar. 2014, pp. 606-618.

European Patent Office, International Search Report for PCT/US2016/028787, dated Jul. 18, 2016.

European Patent Office, Written Opinion for PCT/US2016/028787, dated Jul. 18, 2016.

European Patent Office, Written Opinion for PCT/US2016/028787, dated May 16, 2017.

European Patent Office, International Preliminary Report on Patentability for PCT/US2016/028787, dated Aug. 17, 2017.

* cited by examiner

*Primary Examiner* — Clare M Perrin

(74) *Attorney, Agent, or Firm* — Christopher P. Demas; Teresan W. Gilbert

(57) ABSTRACT

The disclosed technology relates to water soluble, or partially water soluble, chain transfer agents for preparing water soluble polymers by Reversible Addition-Fragmentation Chain Transfer ("RAFT") polymerization in an aqueous medium.

4 Claims, No Drawings

WATER SOLUBLE CHAIN TRANSFER AGENTS

BACKGROUND OF THE INVENTION

The disclosed technology relates to water soluble, or partially water soluble, chain transfer agents for preparing water soluble polymers by Reversible Addition-Fragmentation Chain Transfer ("RAFT") polymerization in an aqueous medium.

Many references for Reversible Addition-Fragmentation Chain Transfer ("RAFT") polymerizations involving Chain Transfer Agents ("CTA") teach polymerizations done in organic solvents such as toluene or 1,4-dioxane in order to prepare water-based polymers (meaning either water soluble polymers or emulsions). While such organic solvents are certainly sufficient for polymerization, they pose both a health risk and a fire hazard, and thus large scale commercialization using such solvents is not desired. Further, when such organic solvent are employed for making water soluble polymers, the organic solvent must be stripped to provide a useful water-soluble polymer, which adds additional hazard as well as time and resources.

A more preferred way of synthesizing water soluble polymers is to make the polymers directly in water with a water soluble CTA. This has been demonstrated many times in the academic literature. In one report, Matsuno, Ryosuke; Goto, Yusuke; Konno, Tomohiro; Takai, Madoka; Ishihara, Kazuhiko *Journal of Nanoscience and Nanotechnology* (2009), 9(1), 358-365, researchers used CTA-Na that was hydrophobically associated to a modified quantum dot (QD) in water to build a QD supported biopolymer. In this example the researchers took advantage of the surfactant properties of CTA-Na to help stabilize the QD and subsequent polymer that was grown out from the core.

What is needed is an economically feasible way to control polymerization of water soluble monomers such as AMPS™, acrylamide, acrylic acid, etc., in aqueous solutions.

SUMMARY OF THE INVENTION

The disclosed technology, therefore, solves the problem of performing living polymerizations in aqueous media by providing water soluble CTAs.

What we are proposing here, is a water soluble CTA-acid, or a water soluble CTA-acid salt made by reacting a CTA-acid with a suitable base, such as sodium hydroxide, or an amine, to produce a water soluble RAFT agent. The molecule is then used to controllably polymerize any water-soluble monomers directly in water. The resulting polymers are of a predetermined molecular weight with a low polydispersity. Since the polymerization is living, water soluble block copolymers and other interesting geometries can be envisioned such as star and comb polymers. These materials have potential applications in any formulation that might require a water soluble polymer of defined molecular weight and shape such as for example, paints and coatings, personal and home care, energy exploration and refinery applications, including but not limited to, water treatment applications, drilling fluids, paraffin inhibiting applications, cementing applications, completion applications, and fuel transportation applications and for improving refinery and oilfield operational efficiencies.

In one aspect, the disclosed technology provides a compound comprising, consisting of, or consisting essentially of a water soluble CTA-acid. In an embodiment, the water soluble CTA-acid can be in the form of a water soluble CTA-acid salt.

In an embodiment, the water soluble CTA-acid can be a thiocarbonate compound of any one of formulas I, II, III or IV:

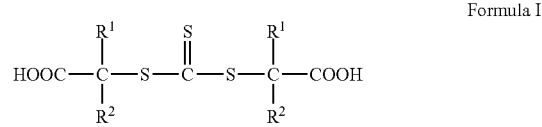

Formula I wherein
each of $R^1$ and $R^2$ is an alkyl group of four carbons or less or H,
so long as the sum of the number of carbon atoms present for all $R^1$, and $R^2$ in formula I together is less than four; or formula II

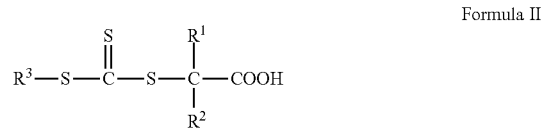

Formula II wherein
each of $R^1$ and $R^2$ is as defined above; and
$R^3$ is an alkyl group of four carbons or less, or H,
so long as the sum of the number of carbon atoms present for all $R^1$, $R^2$ and $R^3$ in formula II together is less than four; or formula III

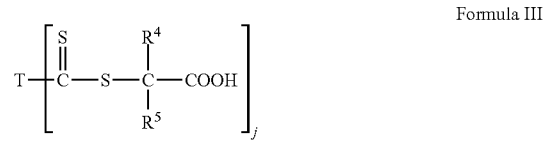

Formula III wherein
each of $R^4$ and/or $R^5$ substituents, independently, comprise an alkyl group having from 1 to 4 carbon atoms, or H;
j is 1 or 2, with the proviso that when j is 1, T is $-(NR^6R^7)$; and when j is 2, T is a divalent radical having a nitrogen atom directly connected to each carbon atom of the two thiocarbonyl groups present;
$R^6$ and $R^7$, independently, are the same or different, and are H or a linear or branched alkyl having from 1 to 4 carbon atoms;
so long as the sum of the number of carbon atoms present for all R substituents in formula III together is less than four; or formula IV

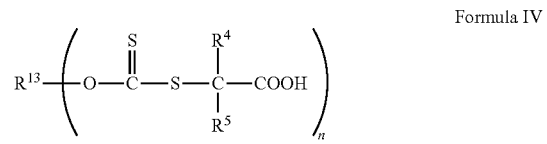

Formula IV wherein
each of $R^4$, and $R^5$ are as defined above
$R^{13}$ is optionally substituted, and is a linear or branched alkyl having from 1 to 4 carbon atoms; and
a is 1 to 4;
so long as the sum of the number of carbon atoms present for all R substituents in formula IV together is less than four.

In another embodiment, the water soluble CTA-acid can be in the form of a water soluble CTA-acid salt, and the CTA-acid portion of the water soluble CTA-acid salt can be a thiocarbonate compound having any of formulas I, II, III, or IV:

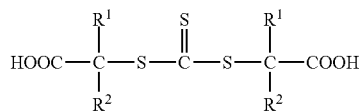

Formula I wherein
$R^1$ and $R^2$, independently, are selected from a linear or branched alkyl having from 1 to 6 carbon atoms, a substituted alkyl having from 1 to 6 carbon atoms, substituted and unsubstituted aryl, $R^1$ and $R^2$ can form a substituted or unsubstituted cyclic ring having from 5 to 12 total carbon atoms; wherein said substituents, independently, are selected from an alkyl having from 1 to 6 carbon atoms, aryl, a halogen which can be the same or different, cyano, an ether having a total of from 2 to 20 carbon atoms, and a nitro group; or formula II

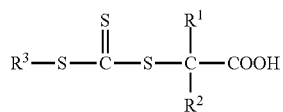

Formula II wherein
$R^3$ is selected from benzyl, a $C_1$ through $C_{18}$ alkyl, a substituted $C_1$ to $C_{18}$ alkyl, wherein said substituted group is selected from halogen, hydroxyl, alkoxy, a $C_1$ to $C_{18}$ hydroxyalkyl, aralkyl, cyanoalkyl, aminoalkyl, carboxylalkyl, carboalkoxyalkyl, and mercaptoalkyl, and wherein $R^1$ and $R^2$, independently, are as described above; or formula III

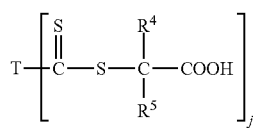

Formula III wherein
j is 1 or 2, with the proviso that when j is 1, T is (—$NR^6R^7$), and when j is 2, T is a divalent radical having a nitrogen atom directly connected to each carbon atom of the two thiocarbonyl groups;
$R^4$ and $R^5$, independently, are the same or different, are optionally substituted as defined for $R^1$ and $R^2$, and are selected from a linear or branched alkyl having from 1 to 12 carbon atoms, aryl having from 6 to 18 carbon atoms, $R^4$ and $R^5$ can form a substituted or unsubstituted cyclic ring having from 3 to 12 carbon atoms, wherein said substituents, independently, are selected from an alkyl having from 1 to 6 carbon atoms, aryl, halogen, cyano, an ether having a total of from 2 to 20 carbon atoms, a nitro group, and combinations thereof; wherein $R^6$ and $R^7$, independently, are the same or different, optionally substituted as defined for $R^1$ and $R^2$, and are selected from hydrogen, a linear or branched alkyl having from 1 to 18 carbon atoms, aryl, aryl alkyl having from 6 to 18 carbon atoms, optionally saturated or unsaturated, arylalkyl having from 7 to 18 carbons, alkenealkyl having from 3 to 18 carbon atoms, polyalkylene glycol ether having from 3 to 200 carbon atoms, and amine, or $R^6$ and $R^7$ can form a cyclic ring with the nitrogen atom having a total of 4 to 12 carbon atoms; or formula IV

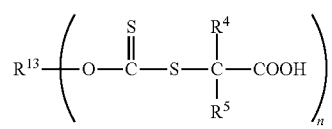

Formula IV wherein
$R^4$ and $R^5$ are as defined above;
$R^{13}$ is optionally substituted, and is selected from linear or branched alkyl having from 1 to 12 carbon atoms, aryl optionally saturated or unsaturated, arylalkyl having from 7 to 18 carbon atoms, acyl, alkene, alkenealkyl having from 3 to 18 carbon atoms, an alkylene group, an alkoxyalkyl, polyalkylene glycol, polyalkylene glycol monoalkyl ether having from 3 to 200 carbon atoms, and 2-trifluoroethyl; wherein when $R^{13}$ is optionally substituted the substituent is selected from alkyl having from 1 to 6 carbon atoms, aryl, halogen, a cyano group, an amino group, an alkene group, an alkoxycarbonyl group, an aryloxycarbonyl group, a carboxy group, an acyloxy group, a carbamoyl group, an alkylcarbonyl group, an alkylarylcarbonyl group, an arylcarbonyl group, an arylalkylcarbonyl group, a phthalimido group, a maleimido group, a succinimido group, amidino group, guanidimo group, allyl group, epoxy group, alkoxy group, an alkali metal salt, a cationic substituent, a hydroxyl group, an ether having a total of from 2 to 20 carbon atoms, nitro, sulfur, phosphorous, a carboalkoxy group, and combinations thereof; and
"a" is 1 to 4.

In an embodiment, the water soluble CTA-acid in the form of a water soluble CTA-acid salt can exclude the CTA-acid portion represented by formula II.

In embodiment of the compound, the water soluble CTA-acid can be in the form of a water soluble CTA-acid salt, and the CTA-acid portion can comprise, consists of, or consist essentially of 2-methyl-2-[(dodecylsulfanylthiocarbonyl) sulfanyl]propionic acid. In another embodiment, the water soluble CTA-acid salt can exclude 2-methyl-2-[(dodecylsulfanylthiocarbonyl)sulfanyl]propionic acid.

In embodiments, the salts of the compounds can be derived from alkali or alkali earth metal hydroxides; alkali earth carbonates; mono-, di-, and/or tri-alkyl-substituted amines; and combinations thereof.

Another aspect of the disclosed technology includes a polymer comprising, consisting of, or consisting essentially of (A) at least one water soluble CTA-acid or CTA-acid salt as described herein, or combinations thereof, and (B) monomer units derived from at least one water soluble monomer. In an embodiment, the polymer can also optionally include (C) monomer units derived from at least one water insoluble vinyl monomer. In an embodiment of the polymer, the water soluble CTA-acid can include a water soluble CTA-acid salt having a CTA-acid portion represented by formula II, and in a particular embodiment, the CTA-acid salt can be the sodium salt of 2-methyl-2-[(dodecylsulfanylthiocarbonyl)sulfanyl]propionic acid.

In an embodiment, the water soluble monomers can comprise, consist of, or consist essentially of AMPS®, acrylic acid, methacrylic acid, itaconic acid, maleic acid, fumaric acid, citraconic acid, mesaconic acid, (alkyl) acrylamide, and derivatives or salts thereof, or any combination thereof. Water insoluble monomers can comprise, consist of, or consist essentially of any polymerizable monomer that includes an alkyl group containing 1-18 carbon atoms consisting of a simple ester, a vinyl ester, a mono-allyl ether, styrene, derivatives thereof, or any combination thereof.

In an embodiment, the polymer can comprise, consist of, or consist essentially of about 0.1 to about 50 weight percent units derived from (A) and from about 50 to about 99.9 percent by weight of the combination of (B) and optional (C).

A further aspect of the disclosed technology includes a process of producing a water soluble polymer. The process can comprise, consist of, or consist essentially of the steps of 1) combining in an aqueous solution a water soluble ethylenically substituted monomer, a CTA-Acid or CTA-acid salt as described herein, or combinations thereof, and a free radical initiator, and 2) free radically polymerizing the water soluble monomers or allowing the water soluble monomers to free radically polymerize. In an embodiment, the process can include producing a macro-CTA-Acid or macro-CTA-Acid salt, and the process can further include adding a water-insoluble monomer to form an oil-in-water emulsion, and further free radically polymerizing the water-insoluble monomer with the macro-CTA-Acid or macro-CTA-Acid salt. In an embodiment of the process, the water soluble CTA-acid can include a water soluble CTA-acid salt having a CTA-acid portion represented by formula II, and in a particular embodiment, the CTA-acid salt can be the sodium salt of 2-methyl-2-[(dodecylsulfanylthiocarbonyl)sulfanyl]propionic acid.

Another aspect of the disclosed technology contemplates the use of a CTA-Acid, CTA-acid salt or mixture thereof as a chain transfer agent. In an embodiment, the water soluble CTA-acid can be used as a chain transfer agent in the form of a water soluble CTA-acid salt having a CTA-acid portion represented by formula II, and in a particular embodiment, the CTA-acid salt can be the sodium salt of 2-methyl-2-[(dodecylsulfanylthiocarbonyl)sulfanyl]propionic acid.

These and other aspects will be described below by way of non-limiting illustration.

DETAILED DESCRIPTION OF THE INVENTION

An aspect of the present technology is directed to a compound comprising, consisting essentially of, or consisting of a water soluble chain transfer agent, also referred to herein as a water soluble CTA-acid. In some embodiments, the CTA-acid is inherently water soluble and in other embodiments, the CTA-acid is prepared into a water soluble salt, also referred to as a CTA-acid salt. As used herein, the term water soluble CTA-acid, or even simply CTA-acid, includes water soluble CTA-acid salts.

As used herein, water soluble means sufficiently miscible to form a 5 wt % solution.

CTA-Acids

Many CTA-acids are known. There are, for example, thiocarbonates, for example, polythiocarbonates such as dithiocarbonate or trithiocarbonate compounds and derivatives thereof. By the term "thiocarbonate", it is meant a compound having at least one segment having the formula:

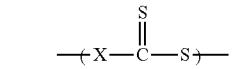

wherein X comprises OR (also referred to herein as "xanthates"), SR (also referred to herein as "carbonates"), or $NR_2$ (also referred to herein as "carbamates"), for example with R being various hydrocarbon, heteroatom and/or hydrogen containing structures or the like preferably as illustrated hereinbelow, but not limited thereto.

Suitable trithiocarbonate compounds for use in the present invention, include, but are not limited to, those disclosed in U.S. Pat. No. 6,596,899 to Lai, herein fully incorporated by reference. In one embodiment, di-acid trithiocarbonate compounds have the following general formula:

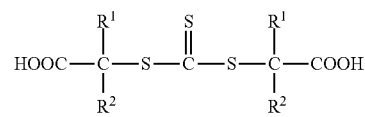

wherein, in one embodiment, $R^1$ and $R^2$, independently, are the same or different, and are hydrogen ("H"), or linear or branched alkyls having from 1 to about 6 carbon atoms, or from 1 to 4 carbon atoms, or a $C_1$ to about $C_6$ alkyl having one or more substituents, or one or more aryls or a substituted aryl group having 1 to 6 substituents on the aryl ring, where the one or more substituents, independently, comprise an alkyl having from 1 to 6 carbon atoms; or an aryl; or a halogen such as fluorine or chlorine; or a cyano group; or an ether having a total of from 2 to about 20 carbon atoms such as methoxy, or hexanoxy; or a nitro; or combinations thereof. Examples of such compounds include s,s'-bis-2-methyl-2-propanoic acid-trithiocarbonate and s,s'-bis-(2-phenyl-2-propanoic acid)-trithiocarbonate. $R^1$ and $R^2$ can also form or be a part of a cyclic ring having from 5 to about 12 total carbon atoms. $R^1$ and $R^2$ are preferably, independently, methyl or phenyl groups. As will be the case for all CTA-acids disclosed herein, the compound represented by the formula will be water-soluble, or at least partially water-soluble depending on the number of carbon atoms in the substituents, and in the case of the formula above specifically, $R^1$ and $R^2$. In a water-soluble embodiment, of the above di-acid thiocarbonate, the sum of the number of carbon atoms present for all $R^1$ and $R^2$ together can be less than 4, or less than 3, with any remainder substituents being H. In such a case, $R^1$ and $R^2$ are preferably, independently, methyl or H groups.

The abbreviated reaction formula for one method for the preparation of s,s'-bis-(α,α'-disubstituted-α''-acetic acid)-trithiocarbonates is generally written as follows:

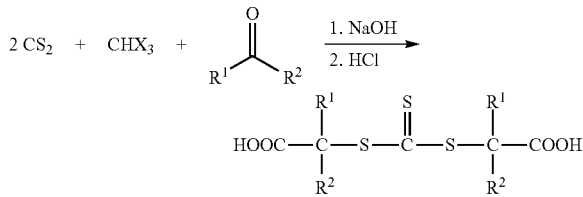

The process utilized to form s,s'-bis-(α,α'-disubstituted-α''-acetic acid)-trithiocarbonate compounds is generally a multi-step process and includes combining the carbon disulfide and a base whereby an intermediate trithio structure is formed. A ketone can serve as solvent for the carbon disulfide/base reaction and thus can be added in the first step of the reaction. In the second step of the reaction, the haloform, or haloform and ketone, or an α-trihalomethyl-α-alkanol are added to the trithio intermediate mixture and reacted in the presence of additional base. The formed reaction product, is subsequently acidified, thus completing the reaction and forming the above described s,s'-bis-(α,α'-disubstituted-α''-acetic acid)-trithiocarbonate compound.

Another aspect of present invention utilizes mono-acid trithiocarbonate compounds having the following formula:

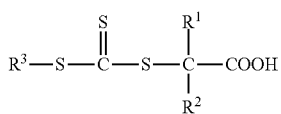

wherein $R^3$ comprises H, a benzyl group, $C_1$-$C_{18}$ or $C_1$-$C_4$ alkyl, or substituted alkyl such as halogen, hydroxyl, or alkoxy, $C_1$-$C_{18}$ hydroxyalkyl, aralkyl, hydroxyalkyl, cyanoalkyl, aminoalkyl, carboxylalkyl, carboalkoxyalkyl or mercaptoalkyl, and $R^1$ and $R^2$ are defined hereinabove. The resulting compound is an s-substituted-s'-(α,α'-disubstituted-α''-acetic acid)-trithiocarbonate, such as, for example, 2-methyl-2-[(dodecylsulfanylthiocarbonyl)sulfanyl]propionic acid. Here again, the compound will be water-soluble, or at least partially water-soluble depending on the number of carbon atoms in the substituents, in this case $R^1$, $R^2$ and $R^3$. In an embodiment, of the mono-acid thiocarbonate, the sum of the number of carbon atoms present for all $R^1$, $R^2$ and $R^3$ together can be less than 4, or less than 3, with any remainder being H. In a water-soluble embodiment, $R^1$, $R^2$ and $R^3$ are preferably, independently, methyl or H groups.

Dithiocarbonate compounds which are utilized in some embodiments of the present invention are disclosed in U.S. application Ser. No. 10/278,335 filed Oct. 23, 2002 and U.S. application Ser. No. 10/681,679 filed Oct. 8, 2003, herein fully incorporated by reference. In one embodiment the dithiocarbamate compounds have the following formula:

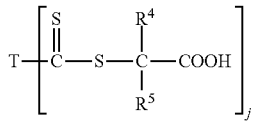

wherein j is 1 or 2, with the proviso that when j is 1, T is $-(NR^6R^7)$; and when j is 2, T is a divalent radical having a nitrogen atom directly connected to each carbon atom of the two thiocarbonyl groups present;
wherein $R^4$ and $R^5$, independently, are the same or different, are H or optionally substituted, and are linear or branched alkyls having from 1 to about 4 carbon atoms, or 1 to about 6 or about 12 carbon atoms; or an aryl group having from 6 to about 18 carbon atoms, optionally containing heteroatoms;
wherein the $R^4$ and/or $R^5$ substituents, independently, comprise an alkyl having from 1 to 4 or 6 carbon atoms; an aryl group; a halogen; a cyano group; an ether having a total of from 2 to about 20 carbon atoms; a nitro; or combinations thereof. $R^4$ and $R^5$ can also form or be a part of a substituted or unsubstituted cyclic ring having from 3 to about 12 total carbon atoms wherein the substituents are described above. $R^4$ and $R^5$, in an embodiment, are, independently, methyl, H, or phenyl groups;
wherein $R^6$ and $R^7$, independently, are the same or different, optionally are substituted, optionally contains heteroatoms; and are H; a linear or branched alkyl having from 1 to 4 carbon atoms, or from 1 to about 18 carbon atoms, an aryl group having from about 6 to about 18 carbon atoms optionally saturated or unsaturated; an arylalkyl having from about 7 to about 18 carbon atoms; an alkenealkyl having from 3 to about 18 carbon atoms; or derived from a polyalkylene glycol ether having from 3 to about 200 carbon atoms. $R^6$ and $R^7$ can also be derived from amines such as, but not limited to, piperazine, morpholine, pyrrolidine, piperidine, 4-alkylamino-2,2,6,6-tetramethyl piperidine,1-alkylamioalkyl-3,3,5,5-tetramethyl-2 piperazinone, hexamethyleneimine, phenothiazine, iminodibenzyl, phenoxazine, N,N'-diphenyl-1,4-phenylenediamine, dicyclohexylamine and derivatives thereof. $R^6$ and $R^7$ can also form a substituted or unsubstituted cyclic ring, optionally containing heteroatoms, along with the nitrogen having a total of from 4 to about 12 carbon atoms, such as benzotriazole, tolyltriazole, imidazole, 2-oxazolidone, 4,4-dimethyloxazolidone and the like. The $R^6$ and $R^7$ substituents, independently, can be the same as described herein with respect to $R^{13}$. $R^6$ and $R^7$ can be, in an embodiment, independently, a phenyl group or an alkyl or substituted alkyl having from 1 to about 18 carbon atoms such as a methyl group, or $R^6$ and $R^7$, independently, can be hexamethylene. In an embodiment, $R^4$, $R^5$, $R^6$ and $R^7$ are, independently, methyl or H groups.

When j is 1, T of the above formula is $-(NR^6R^7)$ and the dithiocarbamate compound is an S-(α,α'-disubstituted-α''-acetic acid) dithiocarbamate generally having the following formula:

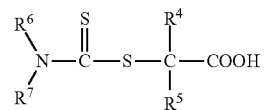

wherein $R^4$, $R^5$, $R^6$, and $R^7$ are as defined hereinabove.

When j is 2, the dithiocarbarbamate compound is a bis-S-(α,α'-disubstituted-α''-acetic acid) dithiocarbamate having the following formula:

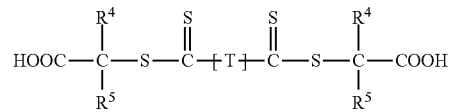

wherein $R^4$ and $R^5$ are defined hereinabove; and
wherein T is a divalent bridging radical having a nitrogen atom directly connected to each of the thiocarbonyl groups present.

In one embodiment T is:

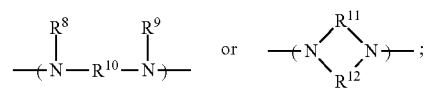

wherein $R^8$ and $R^9$, independently, is the same or different, is optionally substituted, and is H, a linear or branched alkyl having from 1 to 4 carbon atoms, or 1 to about 18 carbon atoms, an aryl group having from about 6 to about 18 carbon atoms, an arylalkyl having from 7 to about 18 carbon atoms, or an alkenealkyl having from 3 to about 18 carbon atoms, wherein the substitutents can be the same as described herein for $R^1$ and $R^2$;

wherein $R^{10}$ is optionally substituted, and is non-existent, or an alkylene group having from 1 to about 18 carbon atoms with about 1 to about 4 or 6 carbon atoms preferred, or derived from a polyalkylene glycol ether having from 3 to about 200 carbon atoms, wherein the substituents can be the same as described herein for $R^1$ and $R^2$ or are heteroatoms such as oxygen, nitrogen, sulfur or phosphorous; and wherein $R^{11}$ and $R^{12}$ independently, is the same or different, and is optionally substituted as described for $R^1$ and $R^2$, and is an alkylene group having from 1 to about 4 carbon atoms, with $R^{11}$ and $R^{12}$ preferably having a collective total of 2 or 3 to 5 carbon atoms.

In further embodiments, T is:

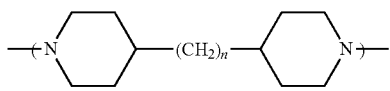

wherein n is 0 to about 18, with 0 or 1 to about 6 preferred;

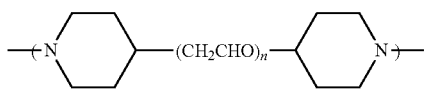

wherein n is 0 to about 18, with 0 to about 6 preferred;

Some specific non-limiting examples of T bridging radicals are:

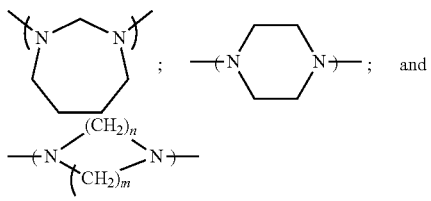

wherein n plus m = 3 to 5;

The S-(α,α'-disubstituted-α"-acetic acid) or bis-S-(α,α'-disubstituted-α"-acetic acid) dithiocarbamates are generally a reaction product of a metal salt of a dithiocarbamate, a haloform, and a ketone. A phase transfer catalyst, solvent, and a base such as sodium hydroxide or potassium hydroxide can also be utilized to form the S-(α,α'-disubstituted-α"-acetic acid) or bis S-(α,α'-disubstituted-α"-acetic acid) dithiocarbamates.

It is to be understood throughout the application formulas, reaction schemes, mechanisms, etc., and the specification that metals such as sodium or bases such as sodium hydroxide are referred to and the application of the present invention is not meant to be solely limited thereto. Other metals or bases such as, but not limited to, potassium and potassium hydroxide, respectively, or combinations thereof are contemplated by the disclosure of the present invention.

Alkoxy dithiocarbonate compounds are utilized in some embodiments of the present invention and having the following general formula, which may be referred to herein as a xanthate,

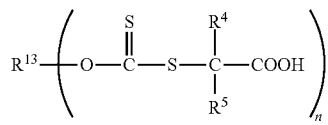

wherein $R^4$ and $R^5$ are as defined hereinabove;

wherein $R^{13}$ is optionally substituted, and can be a linear or branched alkyl having from 1 to 4 carbon atoms, or 1 to about 12 carbon atoms; an aryl group, optionally saturated or unsaturated; an arylalkyl having from 7 to about 18 carbon atoms; an acyl group; an alkenealkyl having from 3 to about 18 carbon atoms; an alkene group; an alkylene group; an alkoxyalkyl; derived from a polyalkylene glycol; derived from a polyalkylene glycol monoalkyl ether having from 3 to 200 carbon atoms; derived from a polyalkylene glycol monoaryl ether having from 3 to 200 carbon atoms; a polyfluoroalkyl such as 2-trifluoroethyl; a phosphorous containing alkyl; or a substituted or unsubstituted aryl ring containing heteroatoms. Alkyl and alkylene groups from 1 to 4 or 6 carbon atoms are preferred;

wherein the $R^{13}$ substituents comprise an alkyl having from 1 to 4 or 6 carbon atoms; an aryl; a halogen such as fluorine or chlorine; a cyano group; an amino group; an alkene group; an alkoxycarbonyl group; an aryloxycarbonyl group; a carboxy group; an acyloxy group; a carbamoyl group; an alkylcarbonyl group; an alkylarylcarbonyl group; an arylcarbonyl group; an arylalkylcarbonyl group; a phthalimido group; a maleimido group; a succinimido group; amidino group; guanidimo group; allyl group; epoxy group; alkoxy group; an alkali metal salt; a cationic substitutent such as a quaternary ammonium salt; a hydroxyl group; an ether having a total of from 2 to about 20 carbon atoms such as methoxy, or hexanoxy; a nitro; sulfur; phosphorous; a carboalkoxy group; a heterocyclic group containing one or more sulfur, oxygen or nitrogen atoms, or combinations thereof; and wherein "a" is 1 to about 4, with 1 or 2 preferred.

The compounds of the above formula are generally identified as O-alkyl-S-(α,α'-disubstituted-α"-acetic acid) xanthates. The O-alkyl-S-(α,α'-disubstituted-α"-acetic acid) xanthates are generated as the reaction product of an alkoxylate salt, carbon disulfide, a haloform, and a ketone. Alternatively, a metal salt of xanthate can be utilized in place of the alkoxylate salt and carbon disulfide.

The general reaction mechanism for forming the O-alkyl-S-(α,α'-disubstituted-α"-acetic acid) xanthates is as follows:

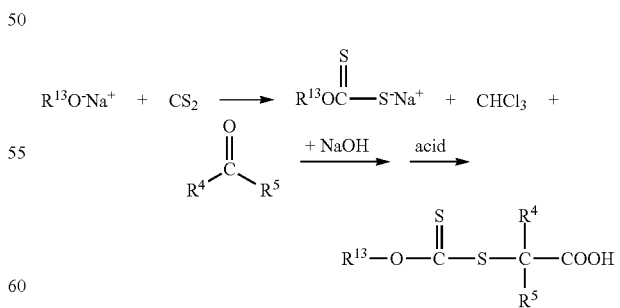

wherein $R^4$, $R^5$, and $R^{13}$ are defined herein.

Salts

The foregoing CTA-acids can be salted, either to impart water-solubility or for ease of use. The salts of the CTA-acid are not particularly limited. Salts can include, for example, alkali or alkali earth metal hydroxides; alkali earth carbonates; mono-, di-, and/or tri-alkyl-substituted amines; and combinations thereof.

In an embodiment, the alkali metal hydroxides can include, but not be limited to, for example, lithium hydroxide, sodium hydroxide, potassium hydroxide. In some preferred embodiments the alkali metal hydroxide salt can comprise, consist essentially of, or consist of sodium hydroxide. In an embodiment, the alkali metal hydroxide can exclude sodium hydroxide, and the resultant polymer can exclude sodium salts.

In an embodiment, the alkali earth metal hydroxides can include, but not be limited to, for example, magnesium hydroxide or calcium hydroxide. Similarly, alkali earth carbonates can include, but not be limited to, for example, magnesium carbonate or calcium carbonate.

Mono, di, and/or tri alkyl substituted amines can include those having an alkyl substitute having from 1 to 12 carbon atoms, or 1 to 8 carbon atoms, or even from 1 to 4 or 6 carbon atoms. The amine can also be an alkanol amine in which the alkyl substituent includes at least one OH group. Particular alkyl amines can comprise, consist essentially of, or consist of any one or more of triethanolamine ("TEA"), ethanolamine, 2-(dimethylamino)ethanol, diethylamine, 2-(2-aminoethoxy)ethanol, 3-amino-1-propanol, N-(2-hydroxyethyl)ethylenediamine.

Polymer

A water soluble form of the CTA-acid or a water soluble CTA-acid in its salt form (i.e., a CTA-acid salt) can be employed to prepare a polymer in an aqueous medium.

The term aqueous medium, or aqueous solution, and the like, means a medium containing a majority of water, optionally along with other water miscible solvents, such as, for example, alcohols and the like. Preferred water miscible solvents include ethyl alcohol, isopropyl alcohol, t-butyl alcohol. Other solvents that may be partially water miscible can include, for example, ethyl acetate, methyl acetate, butyl acetate, benzene, toluene, methyl ethyl ketone, and methylene choride. These solvents also can be used in combination with minor amounts, such as less than 10 volume %, of hydrocarbon solvents such as hexane, cyclohexane, mineral spirits, and the like. A preferred water miscible solvent is isopropyl alcohol. In an embodiment, the aqueous medium consists of water.

Such a polymer would comprise, consist essentially of, or consist of at least one CTA-acid or CTA-acid salt (as the end-cap of the polymer chain), monomer units derived from at least one water soluble monomer, and optionally, monomer units derived from at least one water insoluble vinyl monomer. In an embodiment, the CTA-acid polymer can be made up of about 0.1 to about 49.9 or 50 weight percent, or 0.1 to about 10 or 25 weight percent units derived from a CTA-acid, CTA-acid salt, or combination thereof, but generally from about 0.5 to about 5 weight percent, such as about 1 to about 3 weight percent units derived from a CTA-acid, CTA-acid salt, or combination thereof; and from about 50 to about 99.8 or 99.9 weight percent, or about 75 or even about 90 or 95 to about 99.8 or 99.9 weight percent, or 97 to 99 weight percent of the combination of a water soluble monomer and optional water insoluble vinyl monomer. In an embodiment, the CTA-acid polymer can have about 0.1 to about 49.9 or 50 weight percent, or 0.1 to about 10 or 25 weight percent units derived from a CTA-acid, CTA-acid salt, or combination thereof; from about 50 to about 99.9 percent by weight, or 75 or 90 to about 99.8 or 99.9 weight percent units derived from water soluble monomer, and optionally 0.1 to about 49.9 or 50 weight percent, or from about 0.5 to about 24.9 weight percent, or from about 1 to about 9.9 weight percent units derived from polymerizable water insoluble vinyl monomers.

Water Soluble Monomers

Water soluble monomers that can be included in the polymer are not particularly limited and can comprise, consist essentially of, or consist of any water soluble ethylenically substituted monomer, such as, for example, 2-acrylamido-2-methylpropane sulfonic acid ("AMPS™"), carboxylic acid monomers, ($C_1$-$C_{12}$ alkyl) acrylamide, and derivatives or salts thereof, or any combination thereof.

Water soluble carboxylic acid monomers can include, for example, ethylenically unsaturated polymerizable carboxylic acid monomers. Suitable examples include what are often referred to as carboxylic monomers or acrylate monomers.

Additional examples of suitable sulfonic acid monomers can include: Sipomer COPS®-I, commercially available from Rhodia, which is a 40% aqueous solution of sodium allyl ether sulfonate and sodium 1-allyloxy-2-hydroxypropyl sulfonate, having a molecular weight of about 218; vinyl benzene sulfonic acids, vinyl benzene sulfonates, alkyl vinyl benzene sulfonic acids, alkyl vinyl benzene sulfonates for example SPINOMAR® NaSS, commercially available from Tosoh, which is a sodium p-styrene sulfonate having a molecular weight of about 206; 2-sulfoethylmetahcrylate; alkylvinyl sulfonic acids, alkyl vinyl sulfonates for example sodium vinyl sulfonate (SVS); sodium allylsulfonate (SAS); sodium methally sulfonate (SMAS); dialkylaminoalkyl (meth)acrylate; alkyl or hydrogen halide salts of aminoalkyl (meth)acrylate; hydroxy alkyl(meth)acrylate; or any combination thereof.

In one embodiment, the unsaturated carboxylic monomers can have the following general formulae:

$CH_2=C(CH_3)—COOX$,

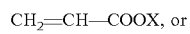
$CH_2=CH—COOX$, or

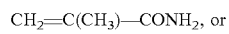
$CH_2=C(CH_3)—CONH_2$, or

$CH_2=CHCONH_2$, wherein X is H; a metal ion such as Li, Na, K, or Ca; an amino group such as an alkylamino or dialkylamino group having from 1 to about 6 carbon atoms or an alkyl/hydrogen halide salt thereof; or hydroxy alkyl group having from 1 to 6 carbon atoms.

Specific water-soluble monomers or co-monomers for use in the present technology include, but are not limited to, the following: acrylic acid, methacrylic acid, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, 2-dimethylaminoethyl acrylate and its alkyl/hydrogen halide salts, 2-dimethylaminoethyl methacrylate and its alkyl/hydrogen halide salts, 2-hydroxyethyl acrylate, hydroxypropyl acrylate (all isomers), hydroxybutyl acrylate (all isomers), polyethylene glycol monoacrylate, polyethylene glycol monomethacrylate, polypropylene glycol monoacrylate, polypropylene glycol monomethacrylate, N,N-diethylaminoethyl acrylate, maleic acid, fumaric acid, itaconic acid, crotonic acid, oleic acid, cinnamic acid, styrene sulfonic acid, and 2-acrylamido-2-methylpropane sulfonic acid (AMPS). Some preferred monomers are AMPS™, acrylic acid, methacrylic acid, and acrylamide.

In some embodiments the water soluble monomers are essentially free of any acrylate monomers. In some embodiments the water soluble monomers are free of any acrylate monomers. In some embodiments the polymers described herein are essentially free of any acrylate monomers. In some embodiments the polymers described herein are free of any acrylate monomers.

In other embodiments the water soluble monomers can include acrylic acid, methacrylic acid, itaconic acid, maleic acid, fumaric acid, citraconic acid, mesaconic acid.

In some embodiments the water soluble monomers can include one or more compounds having the structural formula:

$(R^{12})(R^{13})C=C(R^{14})(R^{15})$ wherein: $R^{12}$ is H or $CH_3$; $R^{13}$ is H or COOH; $R^{14}$ is H or COOH; and $R^{15}$ is H, COOH or $CH_2COOH$; provided that when $R^{12}$ is H and $R^{13}$ is COOH, $R^{14}$ and $R^{15}$ are different and are either H or COOH; when $R^{12}$ and $R^{13}$ are both H, $R^{14}$ is COOH and $R^{15}$ is $CH_2COOH$; and when $R^{12}$ is $CH_3$, $R^{13}$ is COOH and $R^{14}$ and $R^{15}$ are different and are either H or COOH. Suitable examples include maleic acid, itaconic acid, fumaric acid, citraconic acid and mesaconic acid, oleic acid, cinnamic acid or salts thereof. Unsaturated polymerizable monomers containing sulfonic acid or a salts thereof can also be included.

In some embodiments the water soluble monomers can include: (iii) one or more ($C_1$-$C_4$ alkyl or dialkyl) amide monomers. In such embodiments the water soluble monomers may include one or more acrylamide monomers, which may also be described as ethylenically unsaturated amido functional monomers. Suitable examples include acrylamide, methyl acrylamide, methyl methacrylamide, N-alkylmethacrylamide, N,N-dialkylmethacrylamide, N-alkylacrylamide, N,N-dialkylacrylamide, and any combination thereof.

In some embodiments the water soluble monomers can include N,N'-dimethylacrylamide, t-butylacrylamide, t-octylacrylamide, or a combination thereof.

Optional Other Monomers

In an embodiment other monomers, other than the water-soluble monomers described above, are optionally polymerized with the water soluble monomers during a polymerization reaction. Examples of monomers include, but are not limited to, polymerizable water insoluble vinyl monomers, such as any polymerizable monomer that includes an alkyl group containing 1-18 carbon atoms consisting of a simple ester, a vinyl ester, a mono-allyl ether, derivatives thereof, or any combination thereof. Some examples of other monomers include vinyl acetate; styrene; diene monomers having a total of from 4 to 12 carbon atoms with examples including, but not limited to, 1,3-butadiene, isoprene, 1,3-pentadiene, 2,3-dimethyl-1-3-butadiene, 2-methyl-1,3-pentadiene, 2,3-dimethyl-1,3-pentadiene, 2-phenyl-1,3-butadiene, and 4,5-diethyl-1,3-octadiene; α-methyl styrene; and $C_1$-$C_{12}$ alkyl styrenes with substitute groups either on the chain or on the ring or both.

Polymerization Process

A water soluble CTA-acid or a CTA-acid salt, can be employed to polymerize the above monomers in an aqueous medium by a living polymerization process as described hereinbelow to form a CTA-acid polymer.

A living polymerization is a chain polymerization which proceeds in the absence of termination and chain transfer. The following experimental criteria can be utilized to diagnose a living polymerization.

1. Polymerization proceeds until all monomer has been consumed. Further addition of monomer results in continued polymerization.
2. The number average molecular weight, $M_n$ (or $X_n$, the number average degree of polymerization), is a linear function of conversion.
3. The number of polymer molecules (and active centres) is constant and independent of conversion.
4. The molecular weight can be controlled by the stoichiometry of the reaction.
5. Narrow molecular weight distribution polymers are produced.
6. Chain-end functionalized polymers can be prepared in quantitative yields.

Besides those mentioned above, other criteria can also help to determine the living character of polymerization. For radical living polymerization, one is the ability of the polymer isolated from the first step of polymerization to be used as a macroinitiator for the second step of a polymerization in which block copolymers or grafted polymers are ultimately formed. To confirm the formation of block copolymers, measurements of molecular weights and a determination of the structure of the blocks are employed. For structure measurements, the examination of NMR or IR signals for the segments where individual blocks are linked together and a determination of the end groups are both very important. In radical polymerization, only some of the criteria for living polymerizations are actually fulfilled. Due to their ability to undergo further polymerization, these types of polymers can also be called 'reactive polymers'. A more detailed description of living polymerization can be found in "Living Free-Radical Block Copolymerization Using Thio-Inifertors", by Anton Sebenik, Progress in Polymer Science, vol. 23, p. 876, 1998.

The living polymerization processes can be used to produce polymers of narrow molecular weight distribution containing one or more monomers sequences whose length and composition are controlled by the stoichiometry of the reaction and degree of conversion. Homopolymers, random copolymers or block polymers can be produced with a high degree of control and with low polydispersity. Low polydispersity polymers are those with polydispersities that are significantly less than those produced by conventional free radical polymerization. In conventional free radical polymerization, polydispersities (polydispersity is defined as the ratio of the weight average to the number average molecular weight $M_w/M_n$) of the polymers formed are typically greater than 2.0. Polydispersities obtained by utilizing water soluble CTA-acid or CTA-acid salt compounds and derivatives thereof as described herein can be 1.75 or 1.5, or less, often 1.3 or less, and, with appropriate choice of the chain transfer agent and the reaction conditions, can be 1.25 or less.

When the water soluble CTA-acids and CTA-acid salts are utilized only as chain-transfer agents, the polymerization can be initiated with other initiators at lower temperature while yielding polymers with similarly controlled fashion.

Free radical polymerizations utilizing the water soluble CTA-acids and CTA-acid salts as both initiators and chain transfer agents generally form telechelic polymers. When an initiator other than the water soluble CTA-acids and CTA-acid salts is also utilized, a polymer having a single functional end group is formed in proportion to the amount of said other initiator to the water soluble CTA-acids or CTA-acid salts utilized.

The free radical living polymerization process can be applied to any monomers or monomer combinations which can be free-radically polymerized.

In order to initiate the polymerization process, it is often desirable to utilize an initiator as a source for initiating free radicals. Generally, the source of initiating radicals can be any suitable method of generating free radicals such as the thermally induced homolytic scission of a suitable compound(s) (thermal initiators such as peroxides, peroxyesters, or azo compounds), the spontaneous generation from monomer, redox initiating systems, photochemical initiating systems or high energy radiation such as electron beam, X- or gamma-radiation. The initiating system is chosen such that under the reaction conditions there is no substantial adverse interaction of the initiator or the initiating radicals with the transfer agent under the conditions of the experiment. The initiator should also have the requisite solubility in the reaction medium or monomer mixture.

Thermal initiators are chosen to have an appropriate half-life at the temperature of polymerization. The initiators can include one or more of the following compounds: 2,2'-azobis(isobutyronitrile)(AlBN), 2,2'-azobis(2-cyano-2-butane), dimethyl 2,2'-azobisdimethylisobutyrate, 4,4'-azobis(4-cyanopentanoic acid), 1,1'-azobis(cyclohexanecarbanitrile), 2-(t-butylazo)-2-cyanopropane, 2,2'-azobis[2-methyl-N-(1,1)-bis(hydoxymethyl)-2-hydroxyethyl]propionamide, 2,2'-azobis[2-methyl-N-hydroxyethyl)]-propionamide, 2,2'-azobis(N,N'-dimethyleneisobutyramidine)dihydrochloride, 2,2'-azobis(2-amidinopropane)dihydrochloride, 2,2'-azobis(N,N'-dimethyleneisobutyramine), 2,2'-azobis(2-methyl-N-[1,1-bis(hydroxymethyl)-2-hydroxyethyl]propionamide), 2,2'-azobis(2-methyl N-[1,1-bis(hydroxymethyl)ethyl] propionamide), 2,2'-azobis[2-methyl-N-(2-hydroxyethyl) propionamide], 2,2'-azobis(isobutyramide)dehydrate, 2,2'-azobis(2,2,4-trimethylpentane), 2,2'-azobis(2-methylpropane), t-butyl peroxyacetate, t-butylperoxy-2-ethylhexanoate, t-butyl peroxybenzoate, t-butyl peroxyoctoate, t-butylperoxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, dilauroylperoxide, potassium peroxydisulfate, ammonium peroxydisulfate, di-t-butyl hyponitrite, and dicumyl hyponitrite.

Photochemical initiator systems are chosen to have the requisite solubility in the reaction medium or monomer mixture and have an appropriate quantum yield for radical production under the conditions of the polymerization. Examples include benzoin derivatives, benzophenone, acyl phosphine oxides, and photo-redox systems production under the conditions of the polymerization. These initiating systems can include, but are not limited to, combinations of the following oxidants, potassium peroxydisuffate, hydrogen peroxide, t-butyl hydroperoxide and reductants, iron (+2), titanium (+3), potassium thiosulfite, and potassium bisulfite.

Other suitable initiating systems are known to those of ordinary skill in the art, and are described in recent texts. See, for example, Moad and Solomon "The Chemistry of Free Radical Polymerization", Pergamon, London. 1995. pp 53-95.

The preferred initiators of the present technology are 2,2'-azobis[2-mthyl-N(2-hydroxyethyl)propionamide. The amount of initiators utilized in the polymerization process can vary widely as generally from about 0.001 percent to about 99 percent, and desirably from about 0.01 percent to about 50 or 75 percent based on the total moles of CTA-acid or CTA-acid salt utilized. Preferably small amounts are utilized, such as from about 0.1 percent to about 5, 10, 15, 20, or 25 mole percent based on the total moles of CTA-acid or CTA-acid salt. In order to form polymers which are predominately telechelic, initiators other than the thiocarbonate compounds are utilized in lesser amounts, such as from about 0.001 percent to about 5 percent, desirably from about 0.01 percent to about 4.5 percent, and preferably from about 0.1 percent to about 3 percent based on the molar equivalent to the total moles of CTA-acid or CTA-acid salt utilized.

In order to form CTA-acid polymers having monomer repeat units therein, a predetermined amount of CTA-acid or CTA-acid salt, or combination thereof, can be added to a suitable reaction vessel along with a predetermined amount of monomer(s), optional solvent, and optionally initiator. The amount of CTA-acid or CTA-acid salt utilized depends on the desired molecular weight of the polymer to be formed and can be calculated as known to one of ordinary skill in the art. A formula for calculating the amount of CTA-acid or CTA-acid salt (CTA) is as follows:

$$Mn \text{ of polymer} = \left(\frac{\text{Weight of monomer} \times \text{molecular weight of } CTA}{\text{Weight of } CTA}\right) + \text{molecular weight of } CTA$$

The resulting compound can be a macro-CTA-acid monomer, or a polymer or copolymer. The resulting compounds are either telechelic with identical functional groups at the ends of the chain, or a compound having a single functional end group and also an initiator terminated chain (formed by using a conventional initiator such as AlBN). As stated above, the ratios between the resulting polymers can be controlled to give desired results and generally depends on the amount of initiator utilized. The number of repeat groups from all sources, i.e., water soluble, optionally water insoluble and other monomers, or a combination thereof incorporated into each CTA-acid polymer is generally from about 1 to about 400, desirably from about 1 to about 200, and preferably from about 2 to about 80. Inasmuch as one or more water soluble monomers and optionally one or more water insoluble monomers or other monomers which are generally neither hydrophilic or hydrophobic can be utilized, it is to be understood that repeat groups of the polymers or copolymers of the present technology can be the same or different, respectively. That is, random copolymers, terpolymers, etc., can be formed within either of the repeat groups noted, as well as block copolymers which can be formed by initially adding one monomer and then subsequently adding a different monomer (e.g., an internal block copolymer).

The reaction conditions are chosen so that the temperature utilized will generate a radical in a controlled fashion, wherein the temperature is generally from about room temperature to about 200° C. The reaction can be run at temperatures lower than room temperature, but it is impractical to do so. The temperature often depends on the initiator chosen for the reaction, for example, when AlBN is utilized, the temperature generally is from about 40° C. to about 80° C., when azodicyanodivaleric acid is utilized, the temperature generally is from about 50° C. to about 90° C., when di-t-butylperoxide is utilized, the temperature generally is from about 110° C. to about 160° C., when a thiocarbonate is utilized, the temperature is generally from about 80° C. to about 200° C.

The polymerization process of this invention can be carried out in emulsion, solution or suspension, in either a batch, semi-batch, continuous, or feed mode. In the case of emulsion or suspension polymerization, the medium will often be predominately water and conventional stabilizers, dispersants and other additives can be present. For solution polymerization, the reaction medium can be chosen from a wide range of media to suit the monomer(s) being used.

Examples of polymerization mechanisms incorporating water soluble monomers into CTA-acid polymers are as follows:

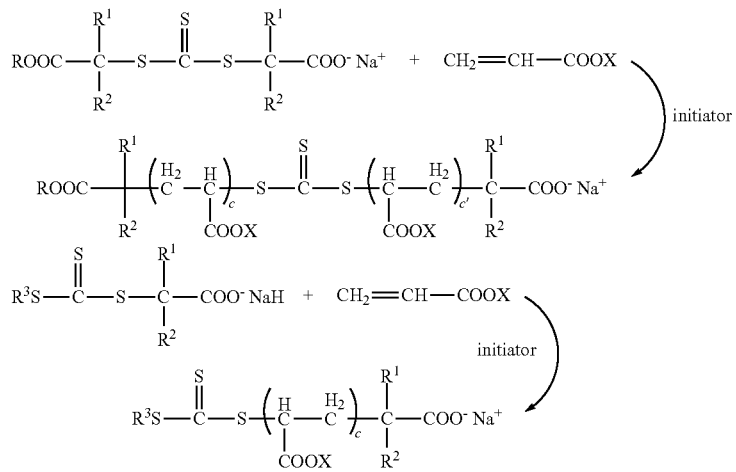

wherein c and c' are each 1 to about 200, and $R^1$, $R^2$, and $R^3$ are defined herein.

Example reaction mechanisms for adding monomers having a hydrophobic group, as well as water soluble monomers to a CTA-acid polymer can include preparing a macro-CTA-acid monomer and adding the water insoluble monomer, as follows:

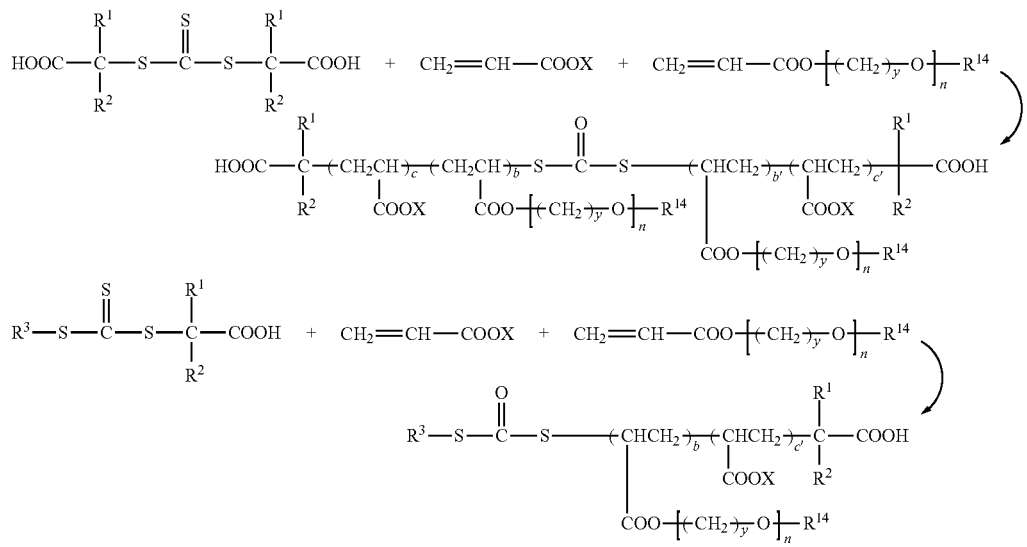

wherein b, b', c, c', n, $R^1$, $R^2$, $R^3$, $R^{14}$ and y are defined herein.

The process disclosed herein can be carried out in emulsion, solution or suspension in either a batch, semi-batch, continuous, or feed mode. Otherwise-conventional procedures can be used to produce narrow polydispersity polymers. For lowest polydispersity polymers, the chain transfer agent is added before polymerization is commenced. For example, when carried out in batch mode in solution, the reactor is typically charged with chain transfer agent and monomer or medium plus monomer. The desired amount of initiator is then added to the mixture and the mixture is heated for a time which is dictated by the desired conversion and molecular weight.

Polymers with broad, yet controlled, polydispersity or with multimodal molecular weight distribution can be produced by controlled addition of the CTA-acid or CTA-acid salt over the course of the polymerization process.

In the case of emulsion or suspension polymerization the medium will often be predominately water and the conventional stabilizers, dispersants and other additives can be present. For solution polymerization, the reaction medium can be chosen from a wide range of media to suit the monomer(s) being used.

As already stated, the use of feed polymerization conditions allows the use of chain transfer agents with lower transfer constants and allows the synthesis of block polymers that are not readily achieved using batch polymerization processes. If the polymerization is carried out as a feed system the reaction can be carried out as follows. The reactor is charged with the aqueous medium, the CTA-acid, CTA-acid salt or combination thereof, and optionally a portion of the monomer(s). The remaining monomer(s) is placed into a separate vessel. Initiator is dissolved or suspended in the reaction medium in another separate vessel. The medium in the reactor is heated and stirred while the monomer+aqueous medium and initiator+aqueous medium are introduced over time, for example by a syringe pump or other pumping device. The rate and duration of feed is determined largely by the quantity of solution the desired monomer/chain transfer agent/initiator ratio and the rate of the polymerization. When the feed is complete, heating can be continued for an additional period.

The water soluble CTA-acids can be employed to prepare polymers for potential applications in any formulation that might require a water soluble polymer of defined molecular weight and shape such as for example, paints and coatings, personal and home care, energy exploration and refinery applications, including but not limited to, water treatment applications, drilling fluids, paraffin inhibiting applications, cementing applications, completion applications, and fuel transportation applications and for improving refinery and oilfield operational efficiencies.

In an embodiment, the water soluble CTA-acids can be employed to prepare improved polymers for use in a method of chelating ions of hardness (e.g., chelating or sequestering metal ions and the like) from a solution.

Typical household and I&I products that may contain polymers of the invention, include, without being limited thereto, fabric care products, such as laundry detergents (powder, liquid, gel, and unit doses) and fabric softeners (liquids or sheets), ironing sprays, dry cleaning aids, anti-wrinkle sprays, stain and spot removers and the like; hard surface cleaners for the kitchen and bathroom and utilities and appliances employed or located therein, such as toilet bowl gels, tub and shower cleaners, hard water deposit removers, floor and tile cleaners, wall cleaners, floor and chrome fixture polishes, alkali-strippable vinyl floor cleaners, marble and ceramic cleaners, air freshener gels, liquid or powder cleaners for dishes (automatic and manual), and the like; disinfectant cleaners, such as toilet bowl and bidet cleaners, disinfectant hand soaps, room deodorizers, heavy duty hand soaps, cleaners and sanitizers, automotive cleaners and the like.

In an embodiment, the improved polymers or solutions thereof are employed in automatic dish detergents. Such dish detergents can be in different forms, such as, for example, liquid, powder, gels, tablets and unit dose pouches, bars, paste, hard or soft compressed monolayered tablet, hard or soft compressed multilayered tablet, single phase unidose detergent, multiphase unidose comprising, for example, any combination of powder, granulate, liquid and gel phases. In another embodiment, the improved polymers can be used in laundry detergents both in liquid, powder, gels, tablets and unit dose pouches, bars, paste, hard or soft compressed monolayered tablet, hard or soft compressed multilayered tablet, single phase unidose detergent, multiphase unidose comprising, for example, any combination of powder, granulate, liquid and gel phases.

Exemplary water treatment applications include, for example, water purification processes for potable & industrial uses, cooling water treatment, boiler water treatment, desalination (e.g., reverse osmosis, distillation), wastewater (e.g., municipal & industrial) treatment, and the like. In one preferred embodiment, the improved polymers are used in water treatment applications as scale inhibitors and/or dispersants.

Exemplary deposit control applications, both scale and suspended solid dispersion, as applied to water treatment including fresh, saline, and process water, include, for example, cooling water treatment, boiler water treatment, thermal and reverse osmosis (RO) desalination, municipal and industrial wastewater, geothermal exploration, oil and gas exploration and production, pulp and paper, sugar refining, as well as mining processes. Scale examples include calcium carbonate; calcium phosphates and phosphonates; calcium, barium, and strontium sulfates; magnesium hydroxide; calcium fluoride; calcium oxalates; silica; and silicates. In some cases, the improved polymers can be used as scale removing agents, rheology modifiers in drilling operations as well as for slurry transport of solids suspended in water.

Exemplary personal care cleansers include but are not limited to shampoos (e.g., 2-in-1 shampoos, conditioning shampoos, bodifying shampoos; moisturizing shampoos, temporary hair color shampoos, 3-in-1 shampoos, anti-dandruff shampoos, hair color maintenance shampoos, acid (neutralizing) shampoos, salicylic acid shampoos, medicated shampoos, baby shampoos, and the like), and skin and body cleansers (e.g., moisturizing body washes, antibacterial body washes; bath gels, shower gels, liquid hand soaps, bar soaps, body scrubs, bubble baths, facial scrubs, foot scrubs, and the like). Similarly, the improved polymer can be employed in pet and animal care applications. Exemplary pet and animal care cleansers include but are not limited to shampoos, medicated shampoos, conditioning shampoos (e.g., detangling, antistatic, grooming), and foaming shampoos.

The amount of each chemical component described is presented exclusive of any solvent or diluent oil, which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

It is known that some of the materials described above may interact in the final formulation, so that the components of the final formulation may be different from those that are initially added. For instance, metal ions (of, e.g., a detergent) can migrate to other acidic or anionic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

The invention herein is useful for preparing RAFT polymers in an aqueous medium, which may be better understood with reference to the following examples.

EXAMPLES

Samples

Formation of CTA-Acid Salt(s)

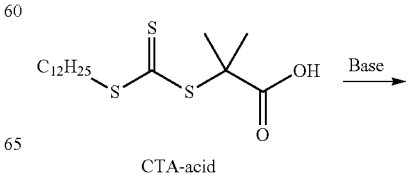

CTA-acid

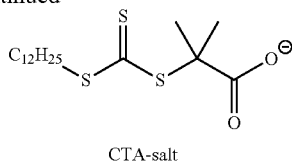

CTA-salt

The following general laboratory procedure was used:
1.) 200 g of water was added to a round bottom flask along with 9 drops of 50 wt. % NaOH in water.
2.) 1.94 g of CTA-acid was added and the mixture gently warmed until dissolved.
3.) pH was adjusted to 7.5
4.) CTA-Na solution was poured into a 1 L 3-necked flask along with 0.55 g Vaso-086 initiator (a 2,2'-Azobis[2-methyl-N-(2-hydroxyethyl)propionamide] available from WAKO Chemicals)
5.) The solution of CTA-Na and initiator was heated to 90° C. and 100 g of a 53 wt. % solution of acrylamide in water was added over 2 hours.
6.) The mixture thickened over time and after addition of all the monomer, solution was held at 90° C. for an additional 2 hrs. before being air cooled to room temperature.

General Polymerization Illustration

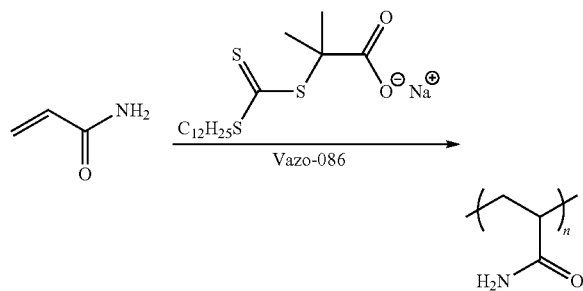

A series of polymerizations was conducted using the general polymerization method listed above. In this series the amount of CTA-Na was varied to produce polyacrylamide) polymers of different molecular weights to demonstrate the controllability of this process to produce defined and predictable molecular weight polymers. The data is shown below in Table 1.

TABLE 1

Polymerization of Acrylamide with varied CTA-Na

| Sample | [CTA-Na] mol/L | [Initiator] mol/L | Conversion (%) | Residual ACM (ppm) | $M_n$* | PDI |
|---|---|---|---|---|---|---|
| 1 | 0.00647 | 0.00477 | 99.88 | 336 | 27,455 | 1.37 |
| 2 | 0.00938 | 0.00477 | 99.86 | 389 | 19,666 | 1.20 |
| 3 | 0.0125 | 0.00477 | 99.78 | 602 | 16,187 | 1.14 |

*$M_n$ determined by GPC using poly(acrylamide) standards

The same general synthetic process as described above was used to polymerize AMPS-Na monomer as well. Again the CTA-Na amount was varied to demonstrate the controllability of this process to produce defined molecular weight polymers. Those results are shown below in Table 2.

TABLE 2

Polymerization a AMPS-Na with varied CTA-Na

| Sample | [CTA-Na] mol/L | [Initiator] mol/L | Conversion (%) | $M_n$ | PDI |
|---|---|---|---|---|---|
| 4 | 0.00647 | 0.00477 | 99.99 | 13,555 | 1.24 |
| 5 | 0.00938 | 0.00477 | 99.99 | 11,979 | 1.21 |
| 6 | 0.0125 | 0.00477 | 100% | 10,902 | 1.3 |

*$M_n$ determined by GPC using poly(acrylamide) standards

Copolymers were produced using the above mentioned polymerization procedure with AMPS-Na (100 g) and acrylic acid (AA—100 g). Random copolymers of AMPS-Na and AA were made by dissolving sodium acrylate in a solution of AMPS-Na (50 wt. % in water). The sodium salt of acrylic acid was used in this case in order to keep the pH of the polymerization mixture above 7. If the pH dips below this value, the CTA will revert back to its acid form and precipitate out of solution leading to uncontrolled polymerization.

Block copolymers were also produced using AMPS-Na and AA. They were also synthesized according to the general polymerization process listed above by building a poly(AMPS-Na) block first, then adding acrylic acid to build a second block, producing poly(AMPS-b-acrylic acid). The results are shown below in Table 3.

TABLE 3

Copolymers of AMPS/Acrylic Acid

| Sample | AMPS/AA (wt %) | $M_n$ | PDI |
|---|---|---|---|
| 7 | 30:70 | 22,784 | 1.54 |
| 8 | 60:40 | 30,544 | 1.64 |
| 9 | 50:50 | 19,829 | 1.44 |
| 10 | 30:70 | 36,316 | 1.64 |
| 11 | 20:80 | 37,087 | 1.62 |
| 12 | 20:80 | 22,962 | 1.50 |
| 13 | 60:40 | 19,028 | 1.47 |
| 14 | 50:50 | 31,464 | 1.65 |

Star polymers were also produced by first forming a homopolymer of either AMPS or acrylamide using the above mentioned process, followed by a cross-linking reaction involving a difunctional monomer such as Bis-acrylamido-2-methylpropane sulfonic acid (BAMPS) or N,N-methylenebisacrylamide (NBAM). Those results are listed below in Table 4.

TABLE 4

Star Polymers of AMPS/Acrylamide

| Sample | Cross-linker | Monomer | Linear $M_n$ | Linear PDI | Star $M_n$ |
|---|---|---|---|---|---|
| 15 | BAMPS | AMPS | 15,346 | 1.35 | 209,165 |
| 16 | NBAM | ACM | 11,144 | 1.15 | 103,502 |

In addition to neutralizing CTA-acid with NaOH to generate the water-soluble chain transfer agent, various amines were used instead of NaOH. These new CTA-"bases" were made using the same procedure shown above ("Formation of CTA-Acid Salt(s)") starting with CTA-acid. The stability of several amines was tested by dispersing CTA-acid in water at 1 wt. % CTA-acid, and then dissolution by adding the amine. The resulting solutions were left at room temperature for 48 hrs. at which point the solubility was checked again. The results are shown below in Table 5.

TABLE 5

Amine Salts of CTA-Acid in Water

| Salt Type | Soluble | Color |
|---|---|---|
| NaOH | yes | yellow |
| Ammonium (NH$_4$)OH | yes | yellow |
|  Jeffamine EDR 148 | no | NA |
| 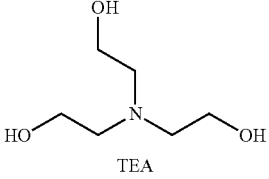 TEA | yes | yellow |
| 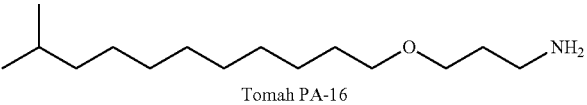 [SMILES: CC(C)CCCCCCCCCOCCCN] Tomah PA-16 | no | NA |
| 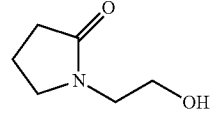 1-(2-hydroxyethyl)-2-pyrrolidone | no | NA |
|  Ethylenediamine | no | NA |
| 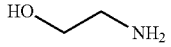 Ethanolamine | yes | orange |
| 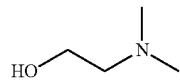 2-(Dimethylamino)ethanol | yes | yellow |
| 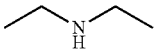 Diethylamine | yes | yellow |
| 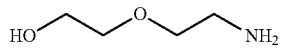 2-(2-aminoethoxy)ethanol | yes | yellow |
|  3-amino-1-propanol | yes | yellow |
| 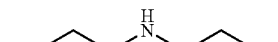 N-(2-hydroxyethyl)ethylenediamine | yes | yellow |

Two of the CTA-amine salts (CTA-TEA and CTA-diethylamine) were chosen to make poly(acrylamide) and poly(AMPS) based on the previously described general polymerization process. Those results are shown below in Table 6.

TABLE 6

Poly(acrylamide) and Poly(AMPS) Using Amine Salts of CTA-Acid

| Sample | Monomer | Amine | $M_n$ | PDI |
|---|---|---|---|---|
| 17 | AMPS-Na | TEA | 14,408 | 1.28 |
| 18 | AMPS-Na | Diethylamine | 11,653 | 1.24 |
| 19 | Acrylamide | TEA | 14,285 | 1.19 |
| 20 | Acrylamide | Diethylamine | 16,037 | 1.16 |

Example 1

The calcium binding ability of the AMPS/AA block copolymers of samples 7 through 14 was tested against the comparative AMPS/AA random copolymers shown in table 7.

| Sample | AMPS/AA (wt %) | $M_w$ |
|---|---|---|
| Comp 1 | 25:75 | <10,000 |
| Comp 2 | 40:60 | ~20,000 |

Calcium binding was determined by preparing 100 mL of a 1 wt % solution of the polymers in water, and adding the solutions to a burette. The polymer solution was then titrated against 100 mL of a standard 0.01M $CaCl_2$ solution. A Ca selective electrode is used to measure the Ca ion signal present in solution (not bound to the polymer). Once the electrode measures 0.00 concentration, all of the Ca ions from the standard have been chelated to the polymer. From there, a calculation can then be performed to determine the amount of polymer needed to bind all of the Ca from the standard solution. The results of the calcium binding tests are shown in Table 8.

TABLE 8

Calcium Binding

| Sample | Ca Binding, mg $CaCl_2$/g of polymer | mg $Ca^{2+}$/g of polymer |
|---|---|---|
| Comp 1 | 303.6 | 110.6 |
| Comp 2 | 310.2 | 113.0 |
| 7 | 688 | 250 |
| 8 | 453 | 165 |
| 9 | 520 | 189 |
| 10 | 691 | 252 |
| 11 | 736 | 268 |
| 12 | 786 | 286 |
| 13 | 505 | 184 |
| 14 | 490 | 179 |

The data in Table 8 shows that the sample polymers prepared with the water soluble CTA-acid bound more calcium than the random copolymers not prepared with the water soluble CTA-acid Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the invention can be used together with ranges or amounts for any of the other elements.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the essential or basic and novel characteristics of the composition or method under consideration.

While certain representative embodiments and details have been shown for the purpose of illustrating the subject invention, it will be apparent to those skilled in this art that various changes and modifications can be made therein without departing from the scope of the subject invention. In this regard, the scope of the invention is to be limited only by the following claims.

What is claimed is:

1. A method of chelating ions of hardness from an aqueous medium comprising adding to an aqueous medium a water soluble polymer comprising (A) at least one water soluble Chain Transfer Agent ("CTA")-acid or CTA-acid salt and combinations thereof, (B) monomer units derived from at least one water soluble monomer, and optionally (C) monomer units derived from at least one water insoluble vinyl monomer
wherein the water soluable CTA-acid comprises a thiocarbonate compound having the formula I

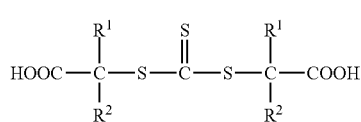

Formula I wherein
each of $R^1$ and $R^2$ is an alkyl group of four carbons or less or H,
so long as the sum of the number of carbon atoms present for all $R^1$, and $R^2$ in formula I together is less than four; or formula II

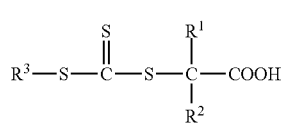

Formula II wherein
each of $R^1$ and $R^2$ is as defined above; and
$R^3$ is an alkyl group of four carbons or less, or H,
so long as the sum of the number of carbon atoms present for all $R^1$, $R^2$ and $R^3$ in formula II together is less than four; or formula III

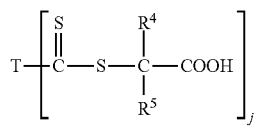

Formula III wherein
each of $R^4$ and/or $R^5$ substituents, independently, comprise an alkyl group having from 1 to 4 carbon atoms, or H;

j is 1 or 2, with the proviso that when j is 1, T is $-(NR^6R^7)$; and when j is 2, T is a divalent radical having a nitrogen atom directly connected to each carbon atom of the two thiocarbonyl groups present;

$R^6$ and $R^7$, independently, are the same or different, and are H or a linear or branched alkyl having from 1 to 4 carbon atoms;

so long as the sum of the number of carbon atoms present for all R substituents in formula III together is less than four; or formula IV

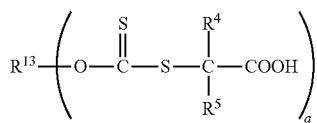

Formula IV wherein
each of $R^4$, and $R^5$ are as defined above $R^{13}$ is optionally substituted, and is a linear or branched alkyl having from 1 to 4 carbon atoms; and a is 1 to 4;

so long as the sum of the number of carbon atoms present for all R substituents in formula IV together is less than four.

2. The method of claim 1, wherein the water soluble monomers comprise 2-acrylamido-2-methylpropane sulfonic acid, acrylic acid, methacrylic acid, itaconic acid, maleic acid, fumaric acid, citraconic acid, mesaconic acid, (alkyl) acrylamide, and derivatives or salts thereof, or any combination thereof.

3. The method of claim 1, wherein the water insoluble monomers comprise any polymerizable monomer that includes an alkyl group containing 1-18 carbon atoms consisting of a ester, a vinyl ester, a mono-allyl ether, styrene, derivatives thereof, or any combination thereof.

4. The method of claim 1 where the polymer is made up of about 0.1 to about 50 weight percent units derived from (A) and from about 50 to about 99.9 percent by weight of the combination of (B) and optional (C).

* * * * *